United States Patent [19]
Van Dijk et al.

[11] Patent Number: 4,894,394
[45] Date of Patent: Jan. 16, 1990

[54] PROCESS FOR THE MANUFACTURE OF METHANOL IN COMBINATION WITH STEAM REFORMING OF LIGHT HYDROCARBONS

[75] Inventors: Arjan Van Dijk; Swan T. Sie, both of Amsterdam, Netherlands

[73] Assignee: Shell Oil Company, Houston, Tex.

[21] Appl. No.: 256,522

[22] Filed: Oct. 12, 1988

[30] Foreign Application Priority Data

Nov. 27, 1987 [GB] United Kingdom ................. 8727774

[51] Int. Cl.$^4$ ............................................. C07C 27/06
[52] U.S. Cl. ..................................... 518/700; 518/704
[58] Field of Search ................................. 518/700, 704

[56] References Cited

U.S. PATENT DOCUMENTS

| | | | |
|---|---|---|---|
| 4,271,086 | 6/1981 | Supp et al. | 518/704 |
| 4,613,623 | 9/1986 | Mahajan et al. | 518/700 |
| 4,614,749 | 9/1986 | Sapienza et al. | 518/700 |
| 4,619,946 | 10/1986 | Sapienza et al. | 518/700 |
| 4,623,634 | 11/1986 | Sapienza et al. | 502/113 |
| 4,628,066 | 12/1986 | Bonnell et al. | 518/700 |

FOREIGN PATENT DOCUMENTS 3244302  5/1984  Fed. Rep. of Germany.

OTHER PUBLICATIONS

T. E. O'Hare et al., "Low Temperature Methanol Process," Am. Chem. Soc. 21st State of Art Symposium, Marco Island, Florida, Jun. 1986.

*Primary Examiner*—Howard T. Mars
*Attorney, Agent, or Firm*—Ronald R. Reper

[57] ABSTRACT

Process for the manufacture of methanol by the reaction of a carbon monoxide and hydrogen mixture obtained by steam reforming of light hydrocarbons in the liquid phase in the presence of the catalyst system obtainable by combination of at least:

(a) the salt containing a cation of a metal of group VIII of the Periodic Table of the Elements,
(b) an alcoholate from an alkaline metal or alkaline earth metal, in a single pass through reactor, by conversion of the hydrogen-carbon monoxide gas mixture, which has been treated after steam treatment of natural gas by scrubbing carbon dioxide from the obtained gas mixture, and which has a hydrogen-carbon monoxide molar ratio in the range of from 2.8–4.5, and using the off-gas from the reaction after recovery of methanol as fuel to the reformer furnace.

7 Claims, 1 Drawing Sheet

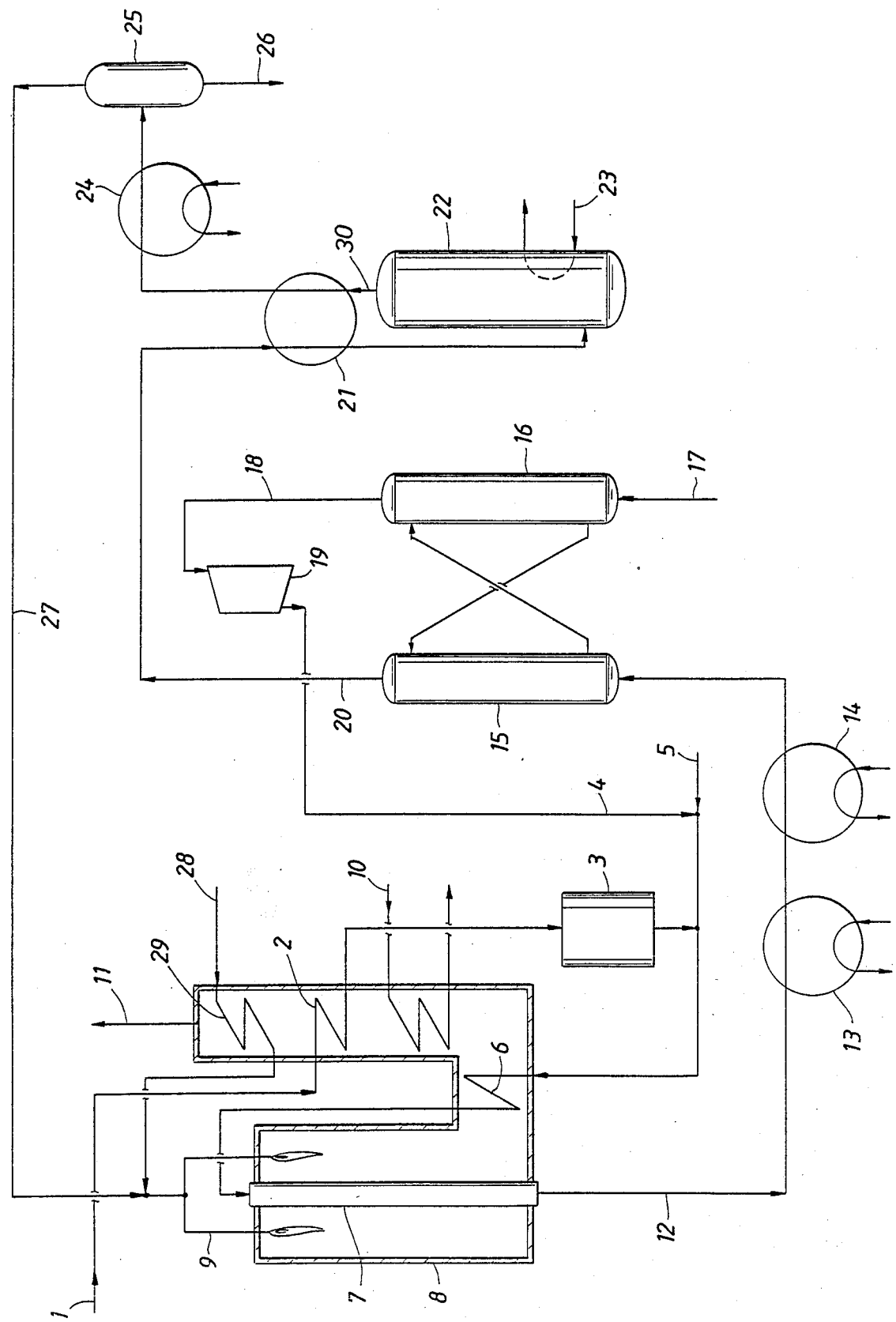

PROCESS FOR THE MANUFACTURE OF METHANOL IN COMBINATION WITH STEAM REFORMING OF LIGHT HYDROCARBONS

BACKGROUND OF THE INVENTION

The invention relates to a process for the manufacture of methanol from carbon monoxide and hydrogen containing mixtures and more particularly to the manufacture of methanol in the presence of a catalyst system, obtainable by combination of at least an alcoholate, derived from an alkali metal or alkaline earth metal, and a salt containing a cation of a metal of Group VIII of the Periodic Table of the Elements and more preferably of nickel, palladium or cobalt.

Embodiments of such a process are in principle known from the U.S. Pat. Nos. 4,613,623, 4,614,749, 4,619,946 and 4,623,634.

In this literature there is commonly disclosed a low temperature methanol preparation process, preferably using a catalyst system comprising sodium hydride-sodium alkanolate, containing 1-6 carbon atoms and nickel(II) acetate, optionally in combination with a metal carbonyl of a group VI metal and more particularly Mo, Cr or W metal, while as most preferred catalyst precursor is proposed a combination of nickel(II) acetate, sodium tert-amyl alcoholate and/or tert-amyl alcohol and sodium hydride.

In these known processes a stoichiometric gas ratio of the carbon monoxide hydrogen starting mixtures is preferred.

Although these catalyst systems on laboratory scale might enable the preparation of methanol in improved yields and under more economical operational conditions (lower temperatures and pressures) as compared to the currently used industrial scale methanol manufacturing processes (operating at high pressures and temperatures, which involve high, economically unattractive equipment and operational costs) they were not applied up to now to industrial scale processes for methanol manufacture.

A problem to be circumvented during evaluation of the laboratory scale processes according to the before-mentioned patent specifications, to an industrial process showing a desired high single pass through conversion is the use of a synthesis gas of stoichiometric hydrogen/carbon monoxide ratio. Such a gas mixture having a ratio in the range of from 1.5-2.5, is usually obtained by partial oxidation of natural gas with pure oxygen. The use of pure oxygen, however, implies the need for an air separation plant, which is costly to build and to operate. A synthesis gas of stoichiometric hydrogen/carbon monoxide ratio, but in a form diluted with nitrogen, can be obtained in an economically more attractive way by partial oxidation of natural gas with air.

However, when using such a nitrogen-diluted gas of stoichiometric ratio of hydrogen and carbon monoxide, in a process for methanol manufacture at economically attractive conversion levels, an off-gas is formed which is difficult to burn due to a too low caloric value, and at less attractive conversion levels a substantially lower yield of methanol is obtained, and substantial proportion of the energy incorporated in the original feedstock is contained in the off-gas in the form of unconverted carbon monoxide and hydrogen. Although this off-gas can now be burned, a good outlet for the energy incorporated in the off-gas will in most cases not be available.

More particularly such an outlet could not be found for a stand-alone process plant for methanol production in a remote location.

On the other hand it is known from e.g. the published German application DE-A-3244302 to produce methanol from a hydrogen and carbon monoxide containing synthesis gas. This synthesis gas produced by steam reforming of natural gas and the like consisting of light hydrocarbons, contains hydrogen in excess of the stoichiometric ratio for methanol formation. Part of the non converted synthesis gas which is recycled to the reactor, is drawn off as off-gas. From this off-gas at least a carbon monoxide containing flow is separated and recycled in the synthesis gas.

It will be appreciated, that the production of gas flows, having the desired hydrogen/carbon monoxide ratio by increasing the carbon monoxide content of the gas, will inevitably be accompanied by significantly cost increasing operations e.g. by the use of membranes, because alternative conversion of hydrogen with inexpensive carbon dioxide, if available, into methanol was surprisingly found not to be applicable with the before described specific catalyst systems. Therefore a person skilled in the art who has to search for an improved, economically attractive industrial process for methanol manufacture, would certainly not be inclined to try primarily to evaluate further the concept of a combination of the before-mentioned low temperature methanol production processes according to U.S. Pat. Nos. 4,613,623; 4,614,749; 4,619,946 and 4,623,634 and steam reforming of light hydrocarbons.

This generally appreciated conception is also actually confirmed by the disclosure in "Low Temperature Methanol Process", T. E. O'Hare et al, Am. Chem. Soc. 21st State of the Art Symposium, Marco Island, Fla., June 1986.

From this publication a clear preference of people skilled in the art can be derived for combinations of low temperature methanol producing processes, using the before described catalyst systems in a liquid form and characterized by much smaller or even completely eliminated recycling of unreacted gas, and partial combustion of natural gas with air, avoiding the use of expensive air separation equipment for the preparation of pure oxygen or oxygen enriched gases, which were necessary to prevent building up of inert nitrogen in the relatively large recycle stream, applied for prior art methanol processes.

Due to the great demand for cheap methanol in very large amounts for application as fuel and as starting material for further chemical syntheses, there is still a strongly urgent need for an economically attractive industrial bulk manufacturing process of methanol, starting from cheap starting materials and operating at attractive economical and environmental conditions, i.e. using rather simple equipment and giving a significant reduction of the methanol cost price.

An object of the present invention is therefore the development of such an industrial process for methanol manufacture.

As a result of extensive research and development a process was found, which meets the hereinbefore mentioned requirements.

SUMMARY OF THE INVENTION

The invention provide a process which comprises reaction of a carbon monoxide and hydrogen containing mixture obtained by steam reforming of light hydrocarbons characterized in that methanol is formed in the liquid phase in the presence of a catalyst system obtainable by combination of at least:

(a) a salt containing a cation of a metal of group VIII of the Periodic Table of the Elements, (b) an alcoholate from an alkaline metal or alkaline earth metal, in a single pass through reactor, by converting a carbon monoxide-hydrogen gas mixture, which has been obtained by steam treatment of natural gas and scrubbing carbon dioxide from the thus produced gas mixture and which has a hydrogen-carbon monoxide molar ratio in the range of from 2.8–4.5, using the off-gas from the reaction, after recovery of methanol, as fuel to the reformer furnace.

BRIEF DESCRIPTION OF THE DRAWING

The drawing shows a schematic flow diagram of a preferred embodiment of the invention.

DESCRIPTION OF PREFERRED EMBODIMENTS

More particularly the process is carried out in one of the preferred embodiments at a temperature in the range of from 70°–140° C. and preferably in the range of from 80°–110° C., and at a operational pressure in the range of from 10–30 bar and more preferably in the range of from 15–25 bar.

According to another preferred embodiment steam reforming of the natural gas is carried out at pressures in the range of from 20–30 bar, while co-formed carbon dioxide is recycled, after having been scrubbed from the gas mixture obtained, to the reformer inlet.

It will be appreciated that the catalyst systems to be used may comprise, in addition to the components (a) and (b), one or more of the following components depending on the specific embodiments of the methanol process:

(c) a hydride of an alkali metal or an alkaline earth metal, (d) an alcohol or an in situ alcohol providing agent. The latter may be any compound which may form in situ an alcohol under the activation conditions and/or reaction conditions of the methanol synthesis and is preferably selected from alkyl formates, alkyl oxalates or alkyl carbonates or mixtures thereof and more preferably formates.

According to an alternative embodiment of the methanol synthesis process, the in situ formation of alcohol may be achieved by addition of a relatively small predetermined amount of water.

The alcohol to be used, if any, is preferably an aliphatic alcohol and more preferably an alkanol. Among the latter, alkanols having 4 to 20 carbon atoms per molecule are preferred, such as tert-butyl alcohol, tert-pentyl alcohol, hexanol or heptanol. Also dihydric alcohols may be used in principle alone or in combination with alkanols.

The alcoholate to be used is preferably a sodium alcoholate or a potassium alcoholate. Among the alcoholates preference is given to alkoxides, particularly to those having in the range of from 1 to 20 carbon atoms per molecule, such as sodium methoxide, sodium ethoxide, sodium propoxide, sodium butoxide, sodium isobutoxide, sodium tert-pentoxide and potassium 2-methyldodec-2-oxide.

The elements of group VIII of the Periodic Table of the Elements that may be used in the salt of component (a) are iron, cobalt, nickel, ruthenium, rhodium, palladium, osmium, iridium and platinum. Strong preference is given to nickel.

The anion of the salt in component (a) may be derived from a great variety of acids. It is preferred that the salt in component (a) is a salt of a carboxylic acid or a sulphonic acid. Among these acids preference is given to alkanoic acids having 1–10 carbon atoms in the chain or to paratoluene sulphonic acid. More preference is given to formic acid, acetic acid and oxalic acid. Component (a) is most preferably nickel formate, nickel acetate, nickel oxalate or nickel tolysate.

The salts in component (a) may contain crystal water, depending on the special composition of the catalyst system.

It will be appreciated that the most attractive features of the process of the present invention, reducing to practice the conception of the present single pass through reactor process for methanol manufacture in an economically optimized combination with steam treatment of natural gas, could certainly not be predicted or expected by people skilled in the art. Namely this before mentioned conception could only be reached after recognition that the synthesis of methanol, using the herein before specified catalysts, is strongly inhibited by the presence of carbon dioxide in the feed gas, and is to proceed in two steps, i.e. formation of a formate ester and more preferably methyl formate (carbonylation step) and subsequent hydrogenation of the ester formed, contrary to different conceptions about this synthesis and the corresponding continuing research efforts by people skilled in the art.

E.g. in connection with the latter conception reference can be made to a vast number of publications and more particularly to page 2, lines 17–26 of published patent application WO 84/00360 and to the before mentioned prior art references.

Very important advantages provided by the process of the present invention from the viewpoint of synthesis, are connected with the use of syngas with excess hydrogen as to the stoichiometric molar ratio.

As the hydrogenation step which constitutes an essential element in the methanol synthesis, when using the specific hereinbefore described catalyst systems has found to be the most difficult one, which benefits from a high hydrogen partial pressure, the overall synthesis of methanol has found to benefit also by the increased hydrogen/carbon monoxide ratio.

The non stoichiometry (i.e. excess hydrogen) has moreover been found to result in stripping off methanol from the catalyst liquid which contained a higher boiling alcohol. Thus, the steady state concentration of methanol is much lower than in a process, using stoichiometric gas mixtures, at high conversion level, while dilution of the catalyst system with methanol was found to be unfavourable for the catalytic activity.

The process of the present invention has the advantage from the reformer view point that methane slip is less critical than in conventional methanol manufacturing processes wherein inerts have to be minimized with regard to the large gas recycling to the reactor. Thus, relatively high reforming pressures without unduly high outlet temperatures are feasible and together with the low pressure of the low temperature methanol synthesis, using the catalysts of the hereinbefore defined type, this obviates the need for usual synthesis gas compressors in conventional methanol processes.

It will be appreciated that a further advantage of the present process is formed by the possibility to balance the energy content of the off gas of the methanol reactor and the energy requirement of the reformer by choice of an appropriate methane slip in the reformer and the level of carbon monoxide conversion in the synthesis.

The invention is further illustrated by the following detailed description of a flow scheme in the figure representing a specific embodiment of the present process, however without restricting the scope of the invention to this specific embodiment.

Natural gas is passed through line 1 to a preheating coil 2 which is situated in the off-gas duct of the steam reformer furnace 8. The preheated natural gas is passed through a desulphurizing section 3, which may consist of a combination of a catalytic hydrodesulfurizing section filled with a conventional hydrodesulfurization catalyst, e.g. a Co/Mo/Al$_2$O$_3$ catalyst and a hydrogen sulphide absorbing unit, such as a zinc-oxide bed.

The desulphurized natural gas is combined with CO$_2$ from a recycle stream led through line 4 and process steam introduced via line 5. The combined natural gas/CO$_2$/steam stream is further preheated through coil 6 before being introduced in the reformer tubes 7. The reformer tubes are filled with a catalyst such as Ni/Al$_2$O$_3$ or a combination of such a catalyst with a similar catalyst promoted with an alkali metal, preferably potassium, placed upstream. The steam reformer tubes are placed inside a furnace heated by burners 9. The combustion gases leaving the reformer are used to preheat the reformer feed gas through the earlier-mentioned heating coils 6 and 2, and to superheat steam through coil 10 and to preheat combustion air introduced via line 28 by means of coil 29 before exiting to the atmosphere via a stack 11.

The reformer product gas leaves the reformer via line 12, is cooled by raising steam in heat exchanger 13 and by preheating boiler feed water in exchanger 14. CO$_2$ is scrubbed from the cooled reformer product gas in scrubber 15 using for instance a solution of an amine such as di-isopropanol amine. The absorber liquid is regenerated in regenerator 16 by stripping with steam introduced via line 17. Desorbed CO$_2$ is led through line 18 to a compressor 19 which raises the pressure to allow reintroduction of the CO$_2$ via line 4 to the reformer feed stream.

The substantially CO$_2$-free synthesis gas stream is led via line 20 and heat exchanger 21 to the methanol synthesis reactor 22 containing the herein before specified catalysts where most of the CO, together with the corresponding amount of H$_2$, is converted to methanol. Reaction heat is largely removed via cooling coil 23. Led by Line 30, the reactor off-gas consisting of methanol vapours, some unconverted CO and the excess amount of H$_2$, is cooled by exchanging heat with the reactor feed stream in heat-exchanger 21 and further cooled in cooler 24. The condensed methanol product is separated from the gas in separator 25 and withdrawn via line 26. The uncondensed gases, comprising mainly excess hydrogen and some unconverted CO are led via line 27 to the burners 9 of the steam reformer furnace where they are combusted with air introduced via line 28 and preheated by preheater 29.

We claim:

1. Process for the production of methanol which comprises:
   (a) reacting a mixture of steam, carbon dioxide and light hydrocarbons at a pressure from 20–30 bar in a reforming zone heated by the oxidation of carbonaceous fuel to obtain steam reformate containing hydrogen and carbon monoxide in a molar ratio of hydrogen to carbon monoxide in the range from 2.8 to 4.5;
   (b) passing said steam reformate to a carbon dioxide separation zone to obtain a carbon dioxide steam and a treated stream reformate stream having substantially less carbon dioxide than said feed to step (b);
   (c) recycling at least part of said carbon dioxide stream from step (b) as feed to step (a);
   (d) reacting said treated stream reformate from step (b) in a single pass through a reaction zone at a temperature in the range from 70°–140° C. and a pressure from 15–25 bar in the presence of a catalyst system resulting from combining
      (1) a nickel salt;
      (2) an alcoholate of an alkali or an alkaline earth metal, and at least one of the following components:
      (3) a hydride of an alkali metal or an alkaline earth metal, or
      (4) an alcohol or an in-situ alcohol providing agent
      to obtain a reaction product containing methanol formed in the liquid phase, carbon monoxide and a mixture of other gases;
   (e) partially condensing said reaction product from step (d) to obtain a methanol product stream and an uncondensed off-gas stream; and
   (f) passing said uncondensed off-gas stream as fuel to heat the reforming zone of step (a).

2. Process according to claim 1 wherein step (c) the reaction

3. Process according to claim 1 wherein said in-situ alcohol providing agent is selected from alkyl formates, alkyl oxalates or alkyl carbonates and mixtures thereof.

4. Process according to claim 3 wherein said in-situ alcohol providing agent is a formate.

5. Process according to claim 1 wherein component (a) is selected from nickel formate, nickel acetate, nickel oxalate and nickel tolysate.

6. Process according to claim 1 wherein catalyst component (b) is a sodium alcoholate or potassium alcoholate.

7. Process according to claim 6 wherein said component (b) is selected from sodium methoxide, sodium ethoxide, sodium propoxide, sodium butoxide, sodium isobutoxide, sodium tert-pentoxide and potassium 2-methyldodec-2-oxide.

* * * * *